United States Patent [19]

Franciose

[11] Patent Number: 5,077,769
[45] Date of Patent: Dec. 31, 1991

[54] DEVICE FOR AIDING A RADIOLOGIST DURING PERCUTANEOUS TRANSLUMINAL CORONARY ANGIOPLASTY

[75] Inventor: Barbara D. Franciose, Elk Grove Village, Ill.

[73] Assignee: Siemens Gammasonics, Inc., Hoffman Estates, Ill.

[21] Appl. No.: 657,808

[22] Filed: Feb. 20, 1991

Related U.S. Application Data

[63] Continuation-in-part of Ser. No. 546,473, Jun. 29, 1990.

[51] Int. Cl.⁵ .............................................. H05G 1/64
[52] U.S. Cl. ...................................... 378/99; 358/111; 378/196
[58] Field of Search .......................... 378/99, 195, 196; 358/111

[56] References Cited

U.S. PATENT DOCUMENTS

| | | | |
|---|---|---|---|
| 4,878,115 | 10/1989 | Elion | 378/99 |
| 4,888,794 | 12/1989 | Haaber et al. | 378/99 |
| 4,937,848 | 6/1990 | Horbascheb et al. | 378/99 |
| 4,943,987 | 7/1990 | Asahina et al. | 378/99 |

Primary Examiner—Craig E. Church
Attorney, Agent, or Firm—Mark H. Jay

[57] ABSTRACT

A control panel, which includes a programmable electroluminescent touch screen and a joystick, is mounted so as to be operable by the radiologist during a PTCA procedure. A bedside monitor displays fluoro and roadmap information during the procedure. The radiologist can adjust the relative weight of the roadmap information to the fluoro information by operating the joystick. The system automatically selects the appropriate roadmap based upon the angular orientation of the camera gantry, or alternatively selects the appropriate gantry position to correspond to that used to produce a satisfactory roadmap.

1 Claim, 5 Drawing Sheets

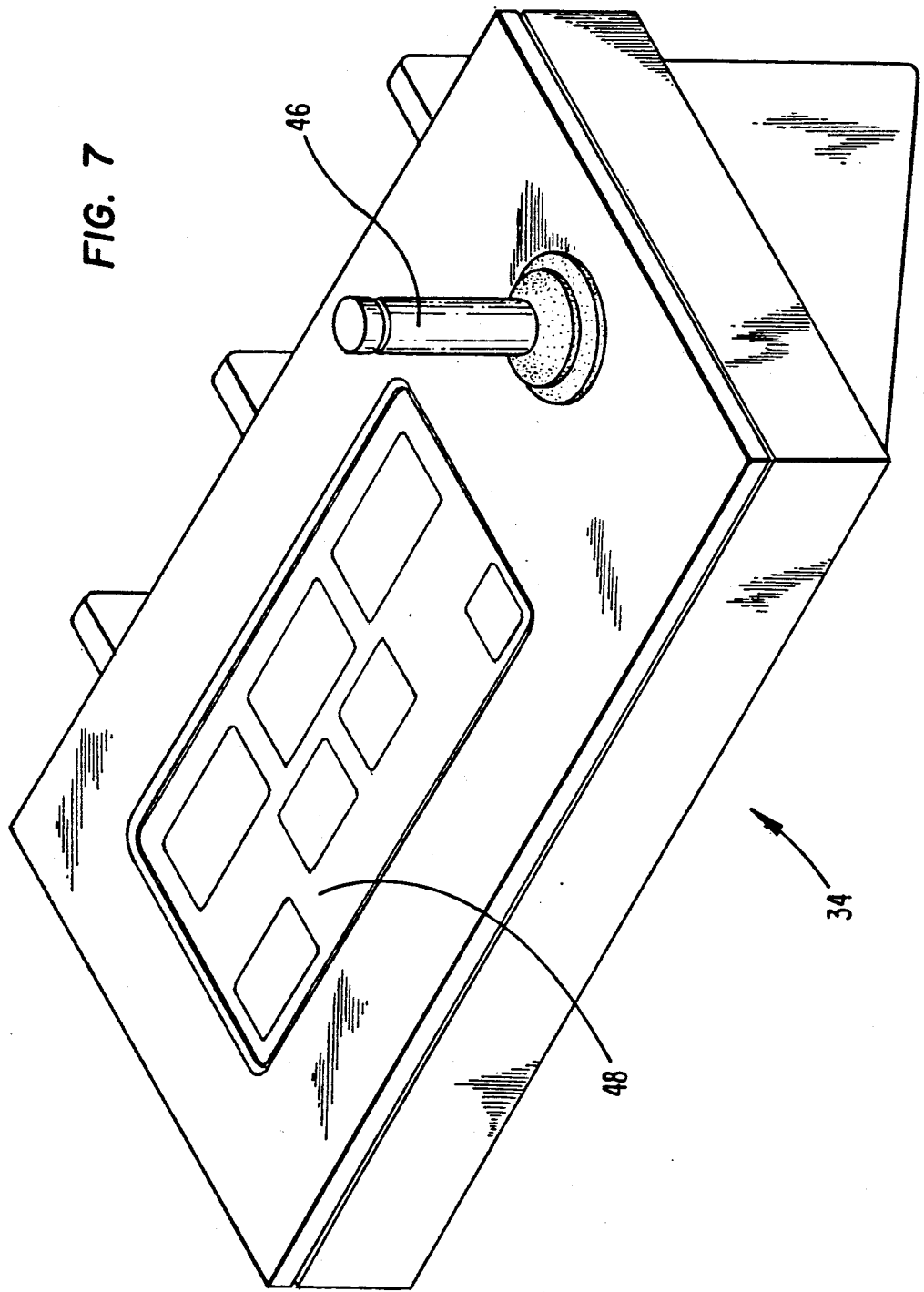

DEVICE FOR AIDING A RADIOLOGIST DURING PERCUTANEOUS TRANSLUMINAL CORONARY ANGIOPLASTY

CROSS-REFERENCE TO RELATED APPLICATION

This is a continuation-in-part of commonly-owned co-pending prior application application Ser. No. 07/546,473, filed June 29, 1990.

BACKGROUND OF THE INVENTION

The invention relates to X-ray apparatus, and more particularly relates to X-ray apparatus which is used during special purpose cardiac catheterization. In its most immediate sense, the invention relates to apparatus which is used during percutaneous transluminal coronary angioplasty (PTCA).

It has long been known that heart function can be impaired by stenotic deposits in the coronary arteries. Such deposits can become relatively large and block blood flow through the artery.

In PTCA, an inflatable catheter is introduced into the patient's circulatory system and guided to a stenosis (blockage) in the patient's heart. When the catheter is properly positioned, it is inflated to a greatly increased size and brought to bear against the stenosis. This causes the stenosis to break up into smaller pieces or to be flattened against the arterial wall, clearing the artery and thereby improving blood flow through it.

X-ray equipment has long been used to aid the PTCA procedure. Ideally, the equipment shows the radiologist or cardiologist where the catheter is actually located. (For the purposes of this disclosure, the difference between a radiologist and a cardiologist is unimportant. In the interest of brevity, the term "radiologist" will be used hereinafter, it being understood that this disclosure applies equally well to cardiologists.) This permits the radiologist to properly guide the catheter to the desired location without e.g. making wrong turns and guiding the catheter in the wrong direction at an arterial fork. Conventionally, as for example in the DIGITRON ® unit sold by Siemens Medical Systems, Inc., a stored opacified image of the relevant portion of the patient's circulatory system (such an image shows the arterial structure and is called a roadmap) is either summed with a real-time fluoroscopic (colloquially, "fluoro") image which includes the catheter or displayed on a separate monitor. The resulting images can be used to guide the catheter to the proper location.

However, existing X-ray equipment suffers from two major disadvantages. First, it is not generally intended for use by the radiologist during the catheterization process and is not easily adapted for use under sterile conditions. This is because conventional equipment uses a keyboard or mouse as a major user interface and such an interface is impractical for a catheterization laboratory.

Second, and equally importantly, conventional X-ray equipment does not present information in such form as would be most useful for the radiologist. Under certain circumstances and in certain stages of the PTCA procedure, the radiologist wishes to see the roadmap of the patient's circulatory system, i.e. the diameter, direction etc. of the artery in which the catheter is being advanced, together with the real-time fluoro image of the catheter and nearby bones and organs. Under other circumstances and in other stages of the PTCA procedure, the radiologist is exclusively interested in the position of the catheter relative to other body structure (bones, organs, etc.) Roadmap information is then irrelevant and distracting.

As a result of such limitations, a PTCA procedure frequently lasts for two hours or more. This is disadvantageous; it is desirable to shorten the duration of any interventional operation. Additionally, since the catheter is in the heart and the patient may have heart distress and require open-heart surgery, an empty operating room is usually held ready until the PTCA procedure is completed. This is quite costly and quite wasteful of limited hospital resources.

It would be advantageous to provide apparatus which could be used by the radiologist during the PTCA procedure to reduce the duration of the PTCA procedure.

One object of the invention is to provide a device which is usable by a radiologist during a PTCA procedure.

Another object of the invention is to provide a device which allows the radiologist to adjust the image information presented to him during a PTCA procedure so as to match the information presented with the information desired.

A further object of the invention is to provide a device which is usable by a radiologist in the sterile conditions of a catheterization laboratory while the radiologist is standing at the patient's bedside.

SUMMARY OF THE INVENTION

In accordance with the invention, there is provided a means for acquiring and storing an opacified image and a means for acquiring a real-time fluoroscopic image. There is also provided a bidirectional means which, depending on operation by the radiologist, either a) selects the opacified image which most closely corresponds, in terms of viewing angle, to the real-time image, or b) adjusts the gantry position to produce a view which is the same as that used to produce the opacified image.

The bidirectional means permits the radiologist to quickly correlate opacified and fluoro images so as to take advantage of the best view available. In a conventional PTCA procedure, the radiologist acquires opacified information from dye injection runs taken at a number of different viewing angles and selects the best image to establish the best viewing angle for use during inflation of the balloon catheter. In accordance with the invention, when the radiologist discovers that a particular gantry position produces satisfactory fluoro images, the opacified image which most nearly correlates with the current fluoro image can be immediately identified and recalled. Alternatively, if he discovers that the viewing angle for a particular opacified image is satisfactory, the gantry can be programmed to replicate the viewing angle so that the opacified and fluoro images will correspond with each other.

BRIEF DESCRIPTION OF THE DRAWINGS

Exemplary and non-limiting preferred embodiments of the invention are shown in the drawings, in which:

FIG. 7 shows the control panel used in the preferred embodiment of the invention.

DETAILED DESCRIPTION OF PREFERRED EMBODIMENTS

It has long been known to use coronary angiography in the catheterization laboratory to aid the PTCA procedure. In coronary angiography, an X-ray source 10 is used to direct X-rays through the patient 12 and a contrast medium (usually, but not necessarily, iodine) which is opaque to X-rays is introduced into the artery of interest and flows along with the bloodstream. The differences in opacity to X-rays is picked up by an image intensifier 16, which produces a visual image from the X-rays which pass through the patient 12.

Figure 1:
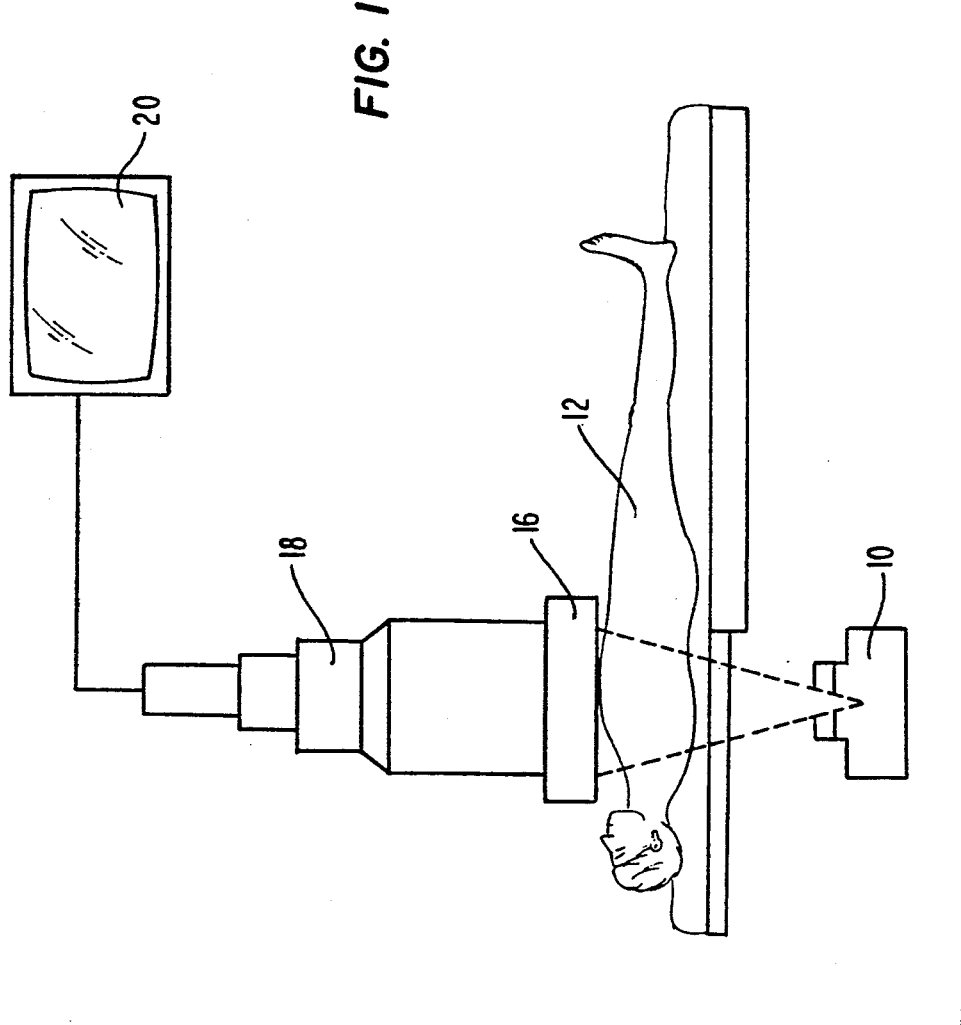
FIG. 1 schematically illustrates angiography apparatus.
Figure 4:
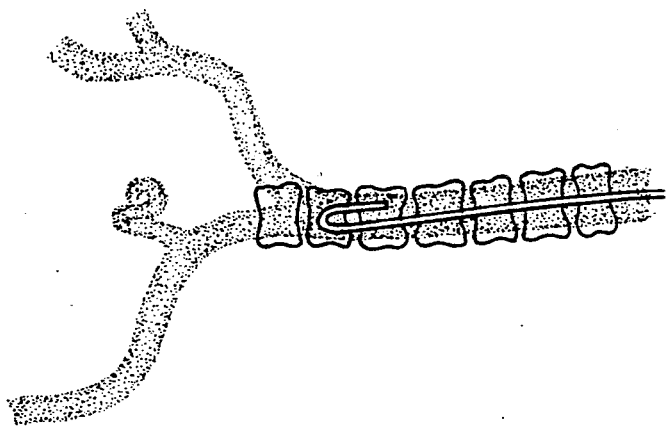
FIG. 4 illustrates a superimposition of FIG. 2 and FIG. 3 in which equal weights are assigned to each.
Figure 3:
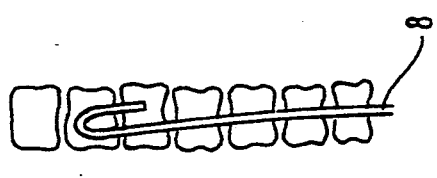
FIG. 3 illustrates a real time fluoroscopic image of a carotid artery.
Figure 2:
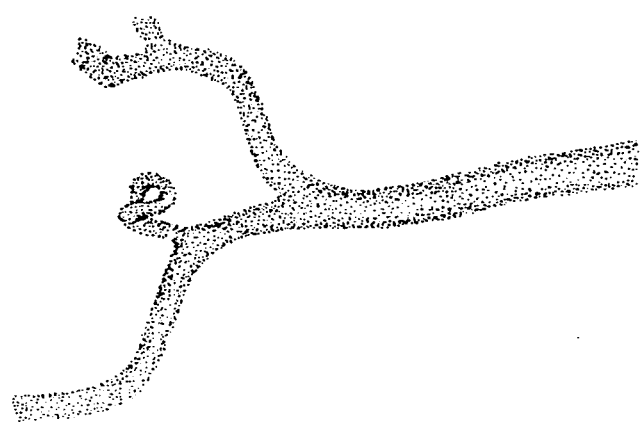
FIG. 2 illustrates an opacified roadmap image of a carotid artery.
Figure 5:
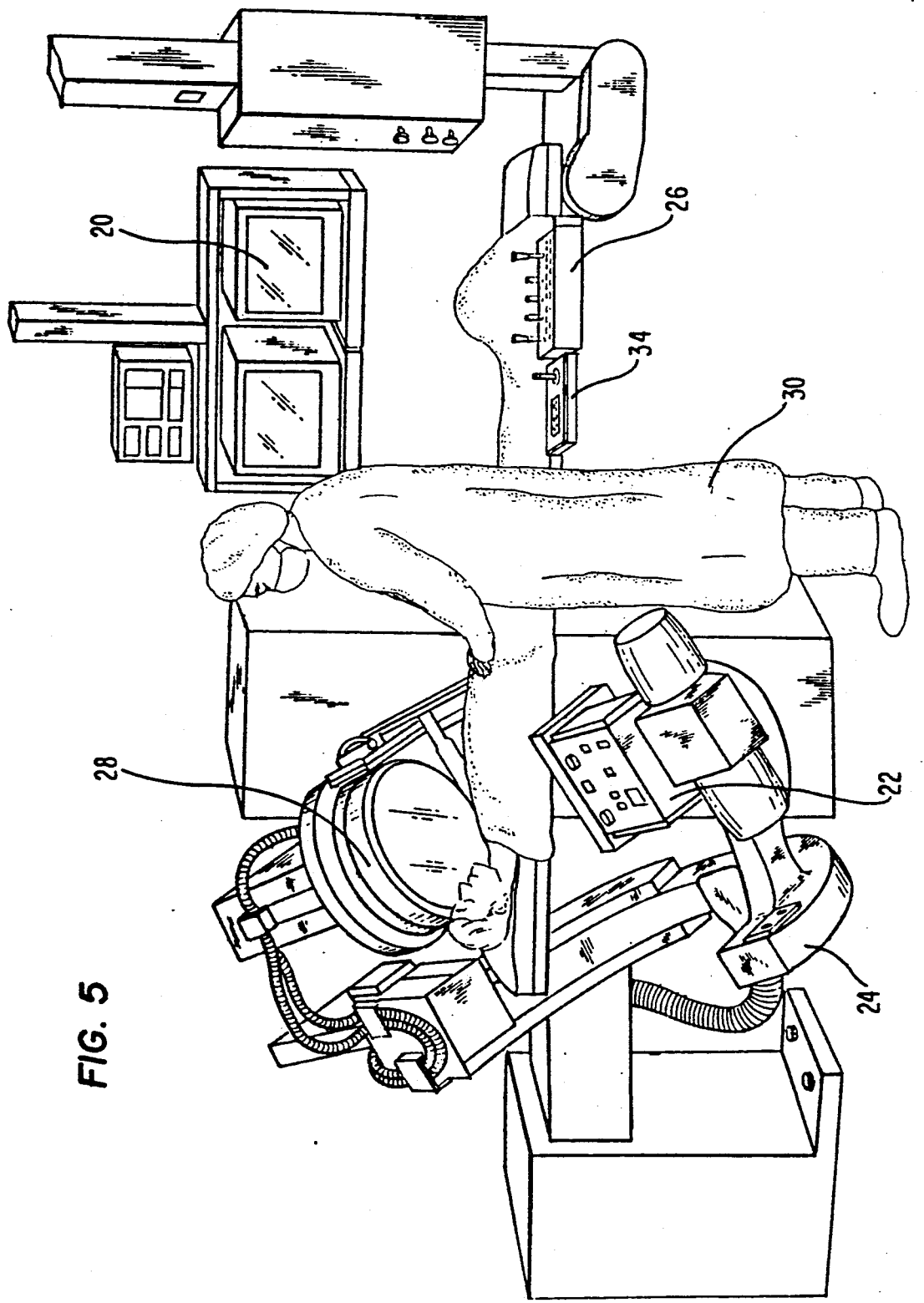
FIG. 5 schematically illustrates the mechanical aspects of a preferred embodiment of the invention.

A video camera 18, mounted in operative relation to the image intensifier 16, converts this visual image into video signals which may eventually be displayed on a monitor 20. Thus, by injecting contrast medium into the coronary arteries of the patient 12, the arterial structure may be visualized on the monitor 20 in a so-called opacified image, or roadmap (FIG. 2). (FIGS. 2, 3 and 4 show a carotid artery even though PTCA is performed on coronary arteries. This is merely for clarity.) This visualization cannot be accomplished directly because blood, by itself, does not show up on an X-ray image.

Let it be assumed that such a roadmap image has been acquired and stored. Let it also be assumed that a catheter 8 has been introduced into the body of the patient 12. The catheter 8 and other non-arterial body structure such as bones, body organs etc. will show up in an X-ray image. If a real-time X-ray image (a so-called fluoro image, FIG. 3) is superimposed (FIG. 4) on the stored opacified image of the artery and displayed on the bedside monitor 20, the radiologist can learn where the catheter 8 is actually located and can advance, redirect and retract it as necessary.

In equipment such as the DIGITRON ® system sold by Siemens Medical Systems, Inc., it is possible to accomplish such superimposition. However, the superimposition is in a fixed weighting. This is disadvantageous because a radiologist will wish to change the display as the PTCA procedure progresses. At the beginning of the operation, the radiologist may wish to see only the real-time fluoro image (e.g. FIG. 3), because he is exclusively interested in the position of the catheter 8 with respect to body landmarks such as bones and organs. In the middle of the operation, the radiologist may wish to see a superimposition image (e.g. FIG. 4) which includes roadmap information and fluoro information, and at the end of the operation, the radiologist may as before only wish to see the real-time fluoro image (FIG. 3). There is no way that the radiologist, by himself, can select between these displays, because a) the control panel of the DIGITRON ® unit is unsuitable for operation by a radiologist who is gloved up and wearing sterile clothing and b) because the software used in the DIGITRON ® unit does not allow such a selection. Thus, any change in display must be accomplished by the equipment operator, responding to verbal instructions from the radiologist. This is unsatisfactory.

Additionally, radiologists actually work by referring alternately to roadmap and fluoro information. This permits them to mentally integrate the two types of information and thereby form an accurate mental impression regarding the progress of the catheter in the artery. It would facilitate such integration if the radiologist were able to fade varying amounts of roadmap information into the real-time fluoroscopic information. This is presently impossible.

In the preferred embodiment of the invention, an X-ray source 22 is mounted to a movable gantry 24, which advantageously although not necessarily is of the C-arm type. The source 22 can be properly positioned relative to the patient 12 by appropriate adjustment of the gantry controls 26.

An image intensifier/video camera 28 is opposed to the source 22 and converts the image into video signals. These are directed to an electronic system 32 (FIG. 6) which is controlled by a control panel 34 (FIG. 7). The control panel 34 is located directly adjacent the gantry controls 26 so as to be conveniently operable by the radiologist 30. The electronic system 32 is connected to the video monitor 20.

Figure 6:
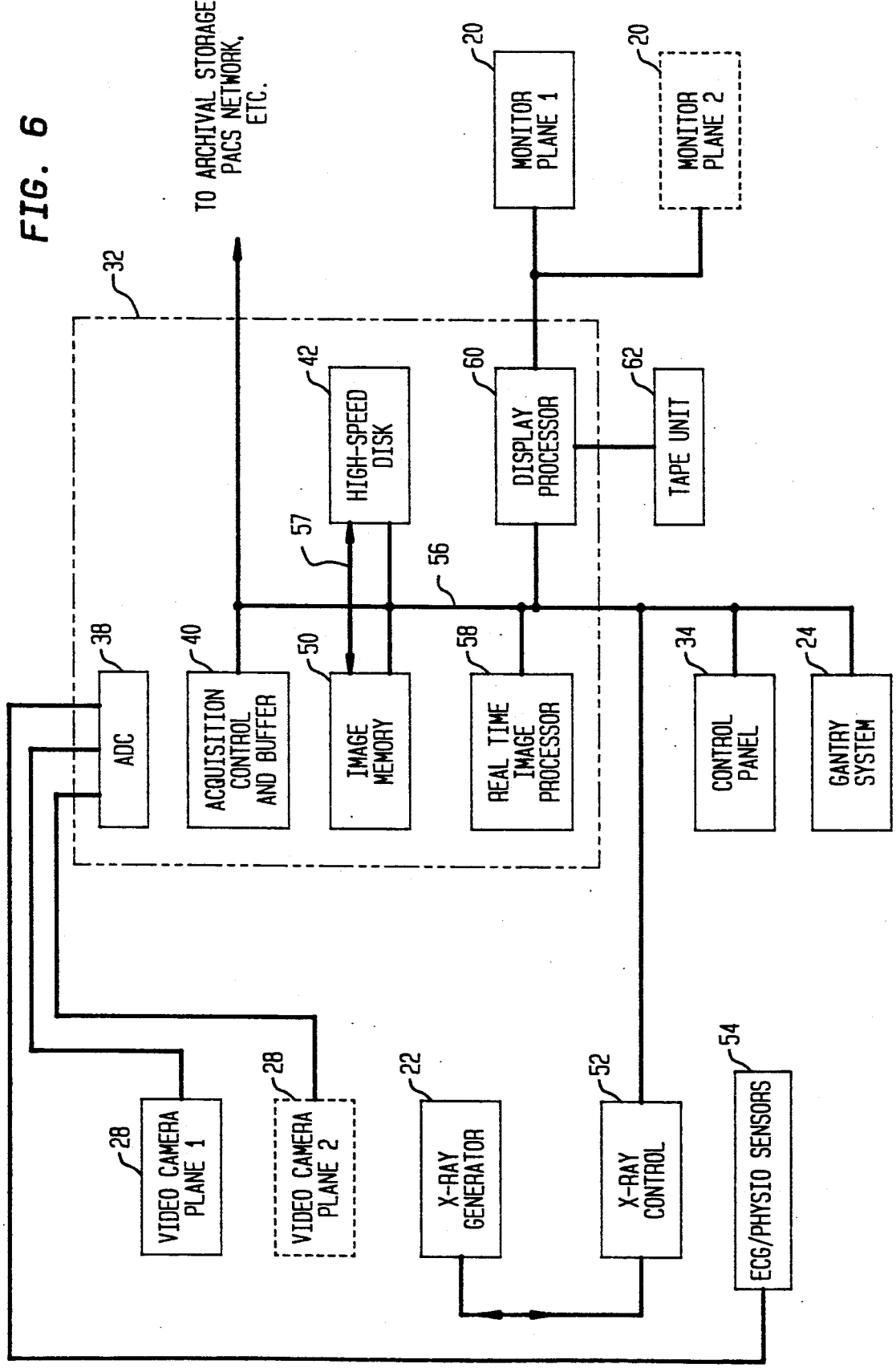
FIG. 6 schematically illustrates the electronic aspects of a preferred embodiment of the invention.

The electronic system 32 will now be briefly described in connection with FIG. 6, which shows the preferred embodiment in the context of a biplane catheterization laboratory. Therefore, two video cameras 28 are shown. In a single plane installation, there would be only one video camera 28; the second video camera 28 is therefore optional and is consequently illustrated in dashed lines.

The electronic system 32 is connected to two video cameras 28 (such as the VIDEOMED ® C cameras sold by Siemens Medical Systems, Inc.), which provide a high resolution (1024×1024) video output. The electronic system 32 is also connected to an X-ray control unit 52 (which may for example be the POLYDOROS ® console and associated X-ray generator 22 sold by Siemens Medical Systems, Inc.) and an ECG/physiological sensor system 54 (such as the MICOR ® system sold by Siemens Medical Systems, Inc.)

Data coming into the electronic system 32 from the cameras 28 and the sensor system 54 is digitized in an analog to digital converter 38 and then routed to acquisition control and buffer circuitry 40. The function of the acquisition control and buffer circuitry 40 is to receive the incoming data and to so control the flow and pipelining of that data so that none is lost.

The acquisition control and buffer circuitry 40 is, like most of the remaining elements, connected to a data bus 56. Also so connected is an image memory 50 which is also connected to a high speed disk 42. The disk 42 receives image data which cannot be retained in the image memory 50, and the disk 42 and image memory 50 are connected together by a direct high speed data path 57. This direct data path 57 permits image data to be shuttled back and forth between the image memory 50 and the disk 42 without being delayed by pipelining in the data bus 56.

A real time image processor 58 is also connected to the data bus 56. The image processor 58 carries out conventional image processing in addition to certain additional functions which are described below. The processed image is routed from the data bus 56 to a display processor 60, which serves to refresh the two monitors 20 and, if this option is elected, to feed a videotape unit 62. (Two monitors 20 are shown because a biplane installation is illustrated. In a single plane installation, only one monitor 20 would be used, and the other monitor 20 is consequently shown in dashed lines.)

The gantry system 24 is connected to the data bus 56. This permits image information to be associated with the gantry configuration that existed at the time the image information was acquired.

The control panel 34 is also connected to the data bus 56. If desired, there may be two control panels 34; one located at bedside and the other located in the control room. Where two control panels 34 are utilized, they are both master/slaved so that both electroluminescent touch screens 48 described below show the same menu screen and messages whenever one of the screens 48 is touched.

When the incoming video is, e.g., an opacified image of a coronary artery under investigation, the image is stored on the disk 42. The gantry system 24 contains position encoders which provide information as to the instantaneous angular orientation of the gantry. Each stored roadmap image on the disk 42 has associated therewith a stored representation of the gantry angle at which the stored roadmap image was acquired. When, later on, a catheter is inserted in the artery, individual X-ray images of the catheter may be acquired in real time, usually by depressing a footswitch (not shown). The real time fluoro images are initially stored in the image memory 50; they are then processed in the image processor 58 as described below. As with the roadmap images, each real-time fluoro image is associated with the gantry angle at which it is taken.

It is known, by itself, to weight and superimpose images on a single video monitor. In accordance with the preferred embodiment of the invention, superimposition of stored opacified images and real-time fluoroscopic images is carried out in the processor 58 and displayed on the monitors 20, but the ratio in which the superimposition is accomplished is, in the appropriate operating mode, controllable by the radiologist by operating the joystick 46 on the control panel 34.

The control panel 34 has a joystick 46 and a programmable electroluminescent touch screen 48. The joystick 46 is spring loaded so as to return to the center position if it is not manually displaced. The touch screen 48 is used to select the operating mode of the preferred embodiment by appropriate menuing. (It will be understood that X-ray equipment must necessarily have provision for, e.g., entering patient information, selecting the particular roadmap which is to be displayed on the monitor 20, etc. For this reason, all X-ray imaging equipment operates in various modes. In the mode herein referenced, which may be termed the "Overlay/Fading" mode, the real-time fluoroscopic information about the catheter is acquired.)

When, e.g. opacified and real-time images are stored respectively on the disk 42 and in the image memory 50, they may be superimposed in various ratios, filtered, etc. in the processor 58. (Image filtering such as high-pass filtering and Sobel edge enhancement is used, for example, to display only edges of blood vessels. This prevents opacified roadmap information from obstructing the real-time fluoroscopic information. Such image filtering is known to persons skilled in the art.) When a real-time fluoro image is to be superimposed with a stored opacified image, the display processor 60 determines the gantry angle at which the real-time image is being taken. The stored gantry angles for the stored opacified images are then compared with the real-time gantry angle and the stored gantry angle most closely corresponding to the real-time gantry angle is determined. The stored opacified image associated with the thus determined stored gantry angle is then superimposed with the real-time fluoro image. The final filtered and superimposed image is stored in the display processor 60 for display on the monitors 20. When the Overlay/Fading mode is selected by touching the appropriate regions of the touch screen 48, up/down positioning of the joystick 46 accomplishes the superimposition of stored and real-time information on an apparently continuous basis.

The radiologist need not, as described above, proceed from a satisfactory real-time fluoro image and cause the best-corresponding opacified image to be retrieved. It is alternatively possible for the radiologist to select the best opacified image. For each such image, the corresponding gantry position may be read out of the high-speed disk 42, routed along the bus 56 and directed to the gantry system 24, causing the gantry system 24 to be brought to that gantry position.

When the unit is in the Overlay/Fading mode, the position of the joystick 46 determines whether the stored roadmap image is faded into or out of the real-time fluoro image, and also determines the rate at which the fading in/out takes place. The rate is determined by the displacement of the joystick 46 from the center position and whether the roadmap information is faded in or out is determined by whether the joystick is up or down relative to the center. Moving the joystick 46 up adds opacified (roadmap) image information (up to a limit of 80% of the superimposition image); the further up the joystick 46 is moved, the faster that the roadmap information is faded in. Moving the joystick 46 down subtracts opacified (roadmap) information from the superimposition image until (in the extreme case) the superimposition image is exclusively composed of real-time fluoroscopic information. As displacement of the joystick 46 from the center increases, so does the rate of subtraction.

The preferred embodiment of the invention does not provide for complete elimination of the real-time information when in the mode herein discussed. This is because the purpose of the Overlay/Fading mode is to permit the radiologist to acquire real-time fluoro information by operating the footswitch (not shown).

The preferred embodiment of the control panel 34 is advantageous because it is easy to operate when in a standing position and dressed and gloved for surgery. To maintain sterility, it may be draped with a thin transparent plastic sheet; this in no way impedes access to the touch screen 48 or joystick 46.

The preferred embodiment described herein is further advantageous in that it makes it easy for the radiologist to select stored opacified images which most nearly correspond to real-time fluoro images, and likewise makes it easy for the radiologist to produce real-time fluoro images which are taken at the same viewing angle as that which produced an advantageous opacified image.

Those skilled in the art will understand that changes can be made in the preferred embodiments here described, and that these embodiments can be used for other purposes. Such changes and uses are within the scope of the invention, which is limited only by the claims which follow.

I claim:
1. A device for use during percutaneous transluminal coronary angioplasty, comprising:
a gantry having mounted thereon an X-ray source and an image intensifier, said source and said intensifier being located in opposition across a patient, said gantry being controllably positionable within an angular configuration;
means for storing a plurality of opacified images obtained from said image intensifier, said storing means being operative to store in association with each of said plurality of opacified images the respective angular configuration of said gantry at which said each of said plurality of opacified images was obtained; and
bidirectional means for a) selecting the opacified image which most closely corresponds, in terms of viewing angle, to the present angular configuration of the gantry and b) adjusting the angular configuration of the gantry to correspond to the angular configuration of the gantry which was used to produce a selected opacified image.

* * * * *